United States Patent [19]
Cornell et al.

[11] Patent Number: 4,702,261
[45] Date of Patent: Oct. 27, 1987

[54] BIOPSY DEVICE AND METHOD

[75] Inventors: William D. Cornell, Ballwin; Richard W. Gilson, Dellwood; Richard A. Burkholder, St. Charles, all of Mo.; Ronald W. Ausherman, Alton, Ill.

[73] Assignee: Sherwood Medical Company, St. Louis, Mo.

[21] Appl. No.: 752,342

[22] Filed: Jul. 3, 1985

[51] Int. Cl.⁴ .............................................. A61B 10/00
[52] U.S. Cl. .................................................... 128/754
[58] Field of Search ............................ 128/749–754, 128/757, 758; 604/160, 164, 165, 166

[56] References Cited

U.S. PATENT DOCUMENTS

| | | | |
|---|---|---|---|
| 2,705,949 | 4/1955 | Silverman | 128/2 |
| 3,400,708 | 9/1968 | Scheidt | 128/757 |
| 3,732,858 | 5/1973 | Banko | 128/753 |
| 3,995,619 | 12/1976 | Glatzer | 128/749 |
| 4,010,737 | 3/1977 | Vilaghy et al. | 128/754 |
| 4,136,095 | 1/1979 | Dafoe | 604/165 |
| 4,396,021 | 8/1983 | Baumgartner | 128/754 |
| 4,457,313 | 7/1984 | Alter | 128/749 |
| 4,461,305 | 7/1984 | Cibley | 128/754 |
| 4,513,754 | 4/1985 | Lee | 128/754 |
| 4,600,014 | 7/1986 | Beraha | 128/754 |

FOREIGN PATENT DOCUMENTS

| | | | |
|---|---|---|---|
| 824449 | 10/1969 | Canada | 128/93 |
| 2462144 | 3/1981 | France | 128/757 |

Primary Examiner—William E. Kamm
Assistant Examiner—Max F. Hindenburg
Attorney, Agent, or Firm—Stanley N. Garber; Andrew J. Beck; William R. O'Meara

[57] ABSTRACT

A biopsy device is provided that includes a housing and relatively slidable tissue cutting and stylet members, both movable with respect to the housing. The members have actuators for manually moving the members and which are mounted in parallel relation to each other and when the proximal ends are equidistant from the housing, the cutting member covers a tissue receiving cavity in the stylet. The actuators are provided with stops to prevent the distal tip of the cutting member from moving distally beyond the distal tip of the stylet. A hand grip can be releasably attached to the device.

13 Claims, 23 Drawing Figures

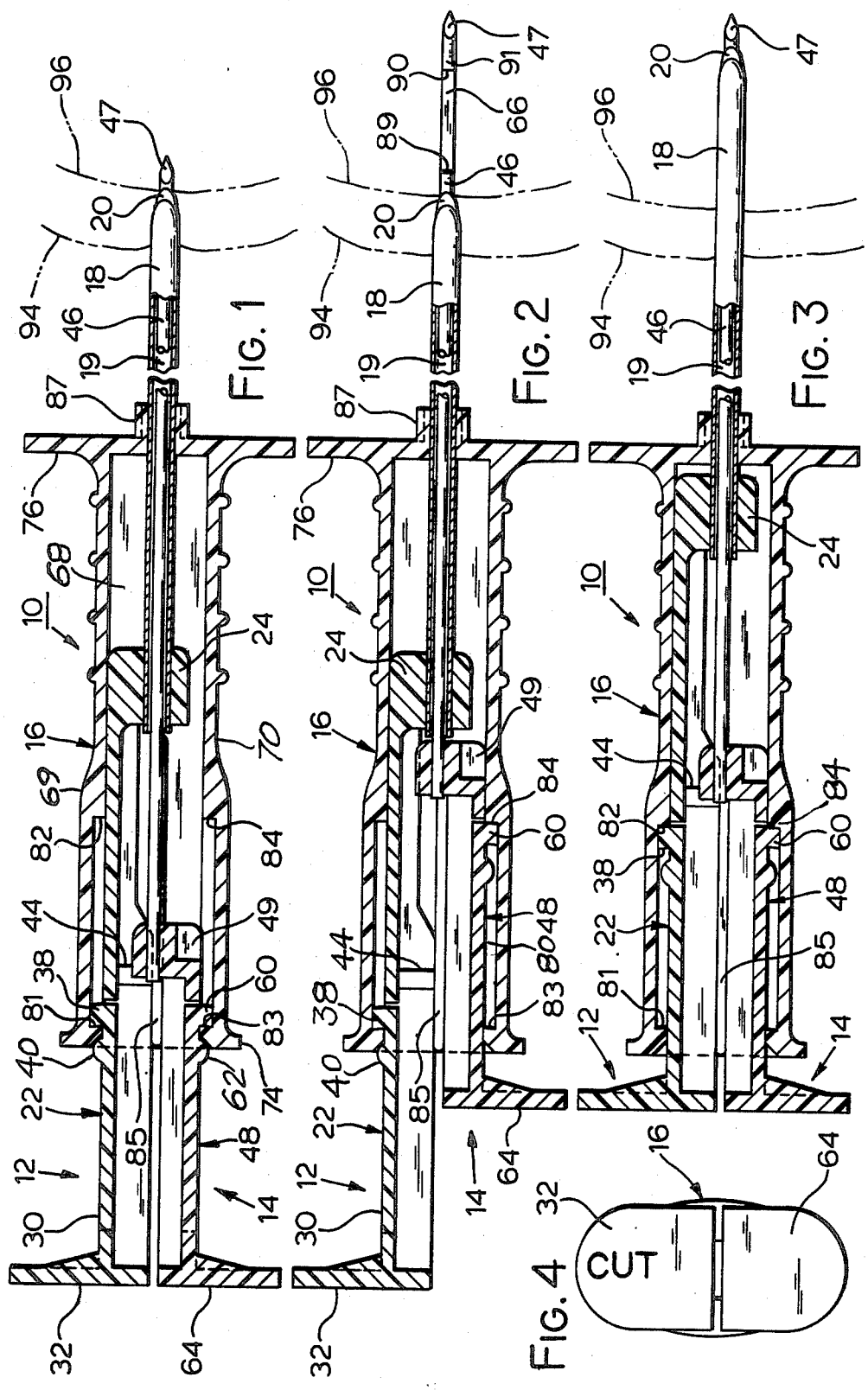

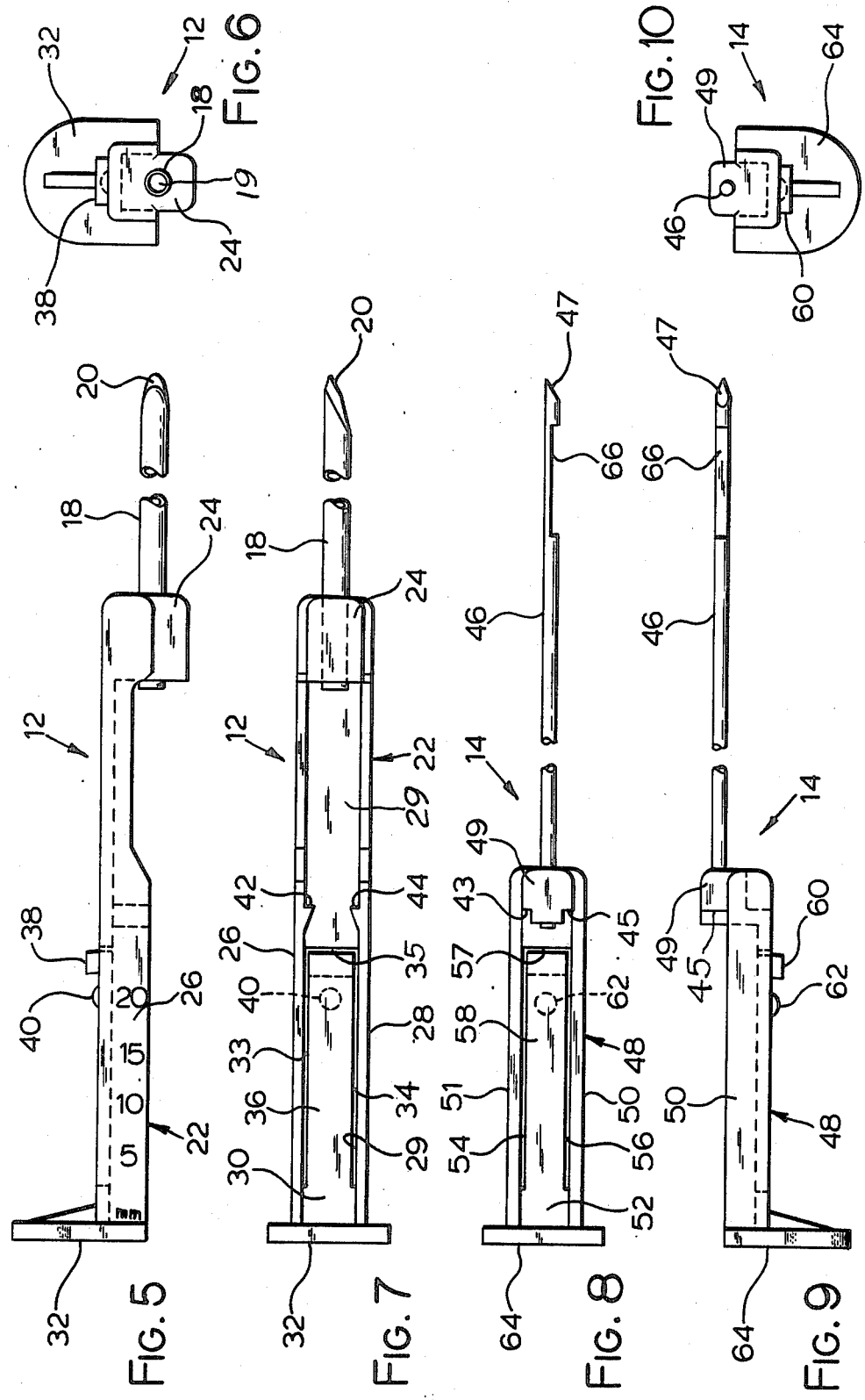

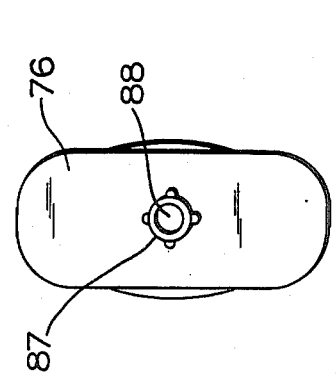
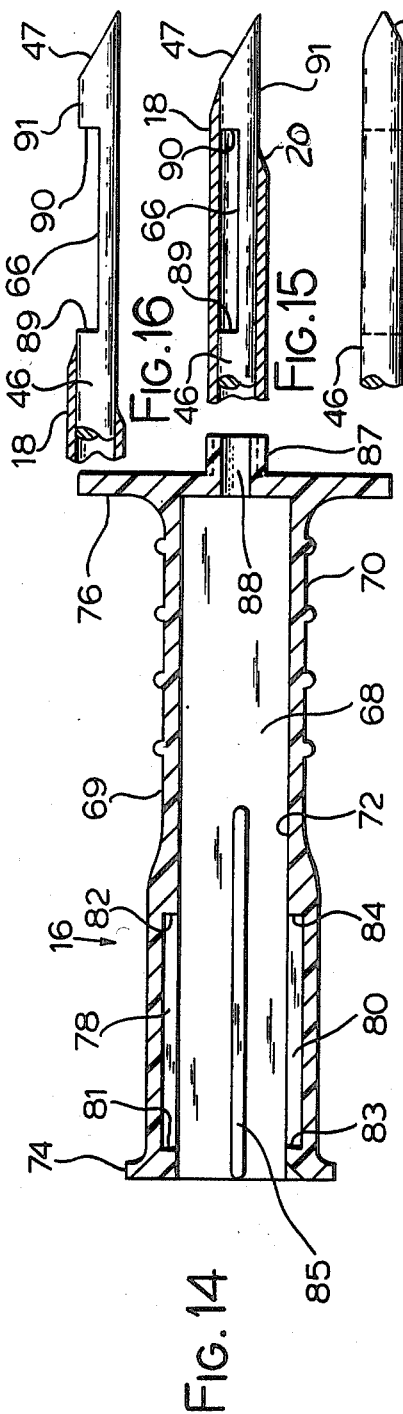
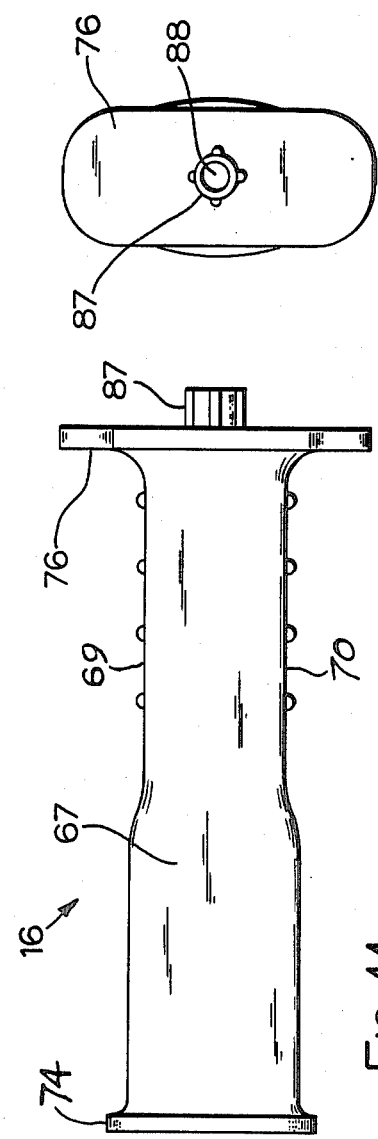
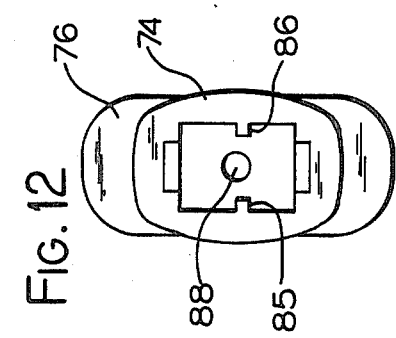

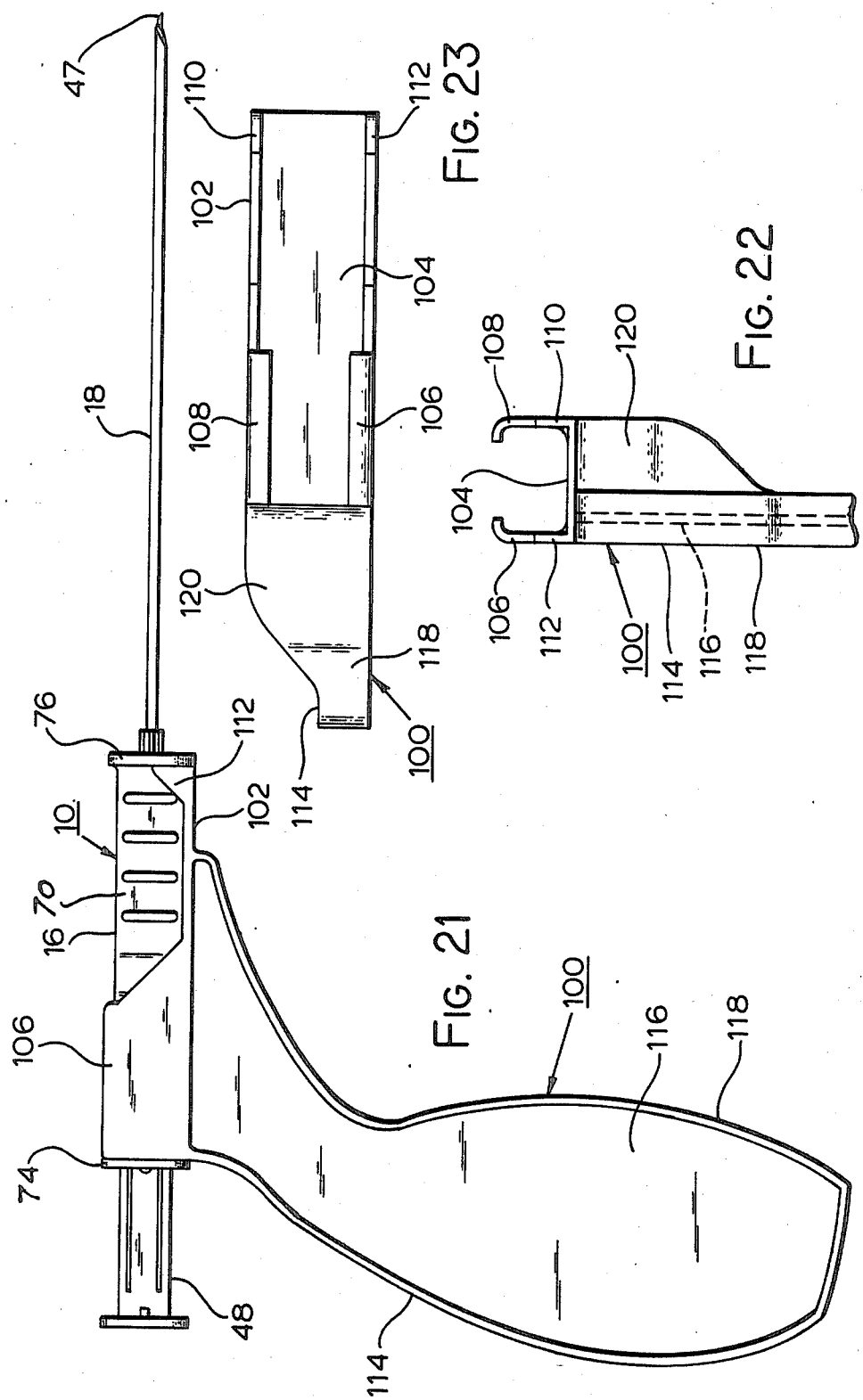

BIOPSY DEVICE AND METHOD

TECHNICAL FIELD

This invention relates to biopsy devices and methods of taking biopsies and more particularly to a biopsy device and a method capable of effecting a subcutaneous biopsy.

BACKGROUND

Some biopsy devices include a tubular cutting element or cannula having a body tissue cutting distal end, and a stylet slidable in the cannula and having a pointed distal end for piercing tissue and a cavity for receiving tissue to be sampled. In using such a device, the stylet and cannula are relatively positioned so that the distal end of the cannula covers the cavity and closely surrounds the distal end of the stylet to prevent the coring of tissue during insertion into the patient. In one method of using such a device, the stylet and cannula are inserted to a position either in the tissue from which a sample is to be taken or to a point adjacent such tissue. The cannula may then be held stationary with one hand, while the stylet is moved distally with the other hand so that the distal end and the cavity of the stylet move into tissue from which a sample is to be taken. Next, the stylet is held stationary with one hand while the cannula is moved distally thereby cutting tissue that has moved into the cavity. With the tissue sample within the cavity and covered by the cannula, the stylet and cannula are removed from the patient. The body tissue sample may then be removed from the biopsy device for testing purposes.

The above procedure is somewhat complicated and there is the danger of inadvertently moving the wrong member at the wrong time. Because the two members are at times movable together and other times movable relative to each other in performing the biopsy, the person performing the biopsy may inadvertently fail to use the proper sequence of movements or steps in effecting the above precedure. This can, in some cases, result in damage to the patient or failure to obtain a sample thereby requiring a second insertion.

With some biopsy devices it is possible to inadvertently insert the cannula and stylet while the cannula cutting tip is distally of the stylet tip and this would result in damage to body tissue due to coring.

SUMMARY OF THE INVENTION

It is therefore an object of the present invention to provide an improved biopsy device wherein one or more of the above problems or disadvantages are overcome.

It is a more specific object to provide a biopsy device which is simpler to use and wherein there is less chance of error in performing the biopsy and therefore less chance of inadvertent damage to the patient.

Still another object is to provide an improved method of obtaining a subcutaneous biopsy.

In accordance with one aspect of the present invention, a biopsy device is provided which includes a cutting member having a cannula which has a distal cutting end, the cannula slidably receiving a stylet having a cavity near the distal end thereof adapted for receiving sample material to be cut by the cannula. The biopsy device includes a housing in which the cannula and stylet members are movable. The device includes means for limiting relative longitudinal movement between the actuators for preventing the distal end of the cutting element for extending distally beyond the distal end of the stylet.

In accordance with another aspect of the invention, a biopsy device is provided which includes a housing, and stylet and cannula members having actuators that are logitudinally slidable relative to each other and the housing, and and are disposed in parallel side-by-side relation. An attachable handle may be used.

In accordance with another aspect of the invention, a method of taking a biopsy sample is provided which includes utilizing a biopsy device having a cannula member with a distal cutting end and a stylet member having a cavity and a tissue piercing distal end. The distal ends are inserted into the patient. While holding the housing stationary with one hand, the stylet is advanced to allow tissue to enter the cavity, and then while holding the housing stationary, the cannula is advanced to sever tissue and provide a tissue sample in the stylet cavity.

These, as well as other objects and advantages of the present invention, will become more apparent from the following detail description and accompanying drawings.

BRIEF DESCRIPTION OF THE DRAWINGS

FIG. 1 is a longitudinal cross-sectional view of a biopsy device in accordance with a preferred embodiment of the present invention;

FIG. 2 is a cross-sectional view similar to FIG. 1 but with the biopsy device in a different operating condition;

FIG. 3 is a view similar to FIG. 1 but with the biopsy device of FIG. 1 in still another operating condition;

FIG. 4 is a left end view of the device of FIG. 1;

FIG. 5 is a top plan view of the cannula member of the biopsy device of FIG. 1;

FIG. 6 is a right end view of the cannula member of FIG. 5;

FIG. 7 is a bottom view of the cannula member as shown in FIG. 5;

FIG. 8 is an upper side view of the stylet member of the biopsy device of FIG. 1;

FIG. 9 is a top plan view of the stylet member of FIG. 1;

FIG. 10 is a right end view of the stylet member of FIG. 9;

FIG. 11 is top plan view of the housing of the biopsy device of FIG. 1;

FIG. 12 is a left end view of the housing of FIG. 11;

FIG. 13 is a right-hand end view of the housing of FIG. 11;

FIG. 14 is a longitudinal cross-sectional view of the housing of FIG. 11;

FIG. 15 is an enlarged fragmentary view of the distal end portions of the stylet and cannula of FIG. 1 rotated 90°;

FIG. 16 is an enlarged fragmentary view of the distal end portions of the stylet and cannula of FIG. 2 rotated 90°;

FIG. 17 is an enlarged bottom view of the distal end portion of the stylet of FIG. 1;

FIG. 21 is a side elevational view of the biopsy device of FIG. 1 on a reduced scale and connected with a handle;

FIG. 22 is a fragmentary right end view of the handle of FIG. 21 with the biopsy device removed; and FIG. 23 is a fragmentary top plan view of the handle of FIG. 21 with the biopsy device removed.

DETAILED DESCRIPTION OF THE PREFERRED EMBODIMENTS

Figure 18:
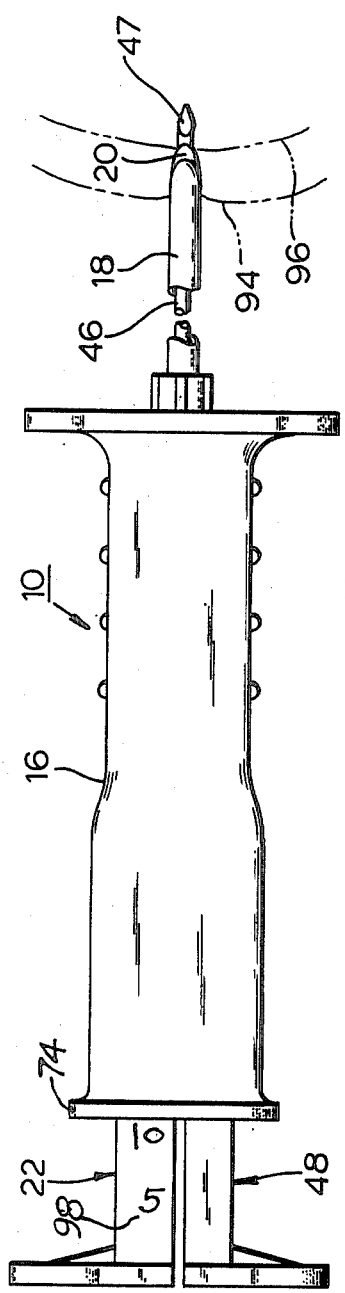
FIG. 18 is a top plan view of the biopsy device of FIG. 1 but with the housing positioned for taking a tissue sample of smaller length.

Referring now to the drawings and more particularly to FIGS. 1–4, a biopsy device 10 is shown including a tissue cutting member 12, a tissue piercing stylet member 14, and a housing 16 receiving the cutting and stylet members 12 and 14 for predetermined sliding movement relative to each other and to the housing 16. The cutting and stylet members are shown in three different relative conditions of operation in FIGS. 1, 2 and 3, which conditions occur during the taking of a biopsy sample. As shown in FIG. 4, the proximal end of cutting member 12 is labelled with the word "Cut" to insure proper identification during use of the biopsy device.

As shown also in FIGS. 5–7, the cutting member 12 includes a tubular cutting element or cannula 18, for example, a stainless steel cylindrical tube having a lumen 19 and a distal cutting end or tip 20. Cutting end 20 is shown pointed and bevel sharpened entirely around the tip for cutting body tissue. The proximal end of cannula 18 is connected to a longitudinal extending actuator 22. Actuator 22 includes a distal end connecting portion 24 which extends normally from the actuator and longitudinal axis of the cannula 18. The proximal end of cutting element 18 is shown extending through the connecting portion 24 and slightly beyond the proximal side of portion 24. Cannula 18 may be fixed to portion 24 by an adhesive such as a cured epoxy resin or by other suitable means.

Actuator 22 has a pair of opposed upper and lower parallel walls 26 and 28, and an outer sidewall 30 effecting a channel 29. At the proximal end of the actuator is a radially outwardly extending flange 32 having a flat proximal side. Sidewall 30 has a pair of longitudinally extending slots 33 and 34 and a cross slot 35 interconnecting slots 33 and 34 to provide a resilient or spring arm 36. Resilient arm 36 is provided with an abutment 38 at the distal end which serves as a stop and which may be generally rectangular as shown. Spaced a small distance proximally of abutment stop 38 is a radially outwardly extending rounded bump 40. On the opposed upper and lower sides 26 and 28 there is provided a pair of abutment stops 42 and 44, respectively, which are adapted to limit relative longitudinal movement between the cutting member 12 and stylet member 14 as will be discussed hereafter.

The stylet member 14, as seen also in FIGS. 8–10, includes an elongate stylet or needle 46 having a pointed sharp distal end 47 for piercing body tissue. The proximal end of needle 46 is connected to a needle actuator 48. Actuator 48 has a inwardly extending distal end portion 49 to which the stylet 46 is fixed, such as by a cured exposy resin or by other suitable means. Actuator 48 includes upper and lower parallel walls 50 and 51, respectively, and an outer sidewall 52 connecting the upper and lower walls so as to form a channel. Wall 52 includes a pair of longitudinally extending slots 54 and 56 and a distal end cross slot 57 connecting slots 54 and 56 to form a resilient spring-like members 58. The resilient member 58 has an integral, rectangular abutment or stop 60 and a bump 62 spaced slightly proximally of the abutment 60. Actuator 48 also has a flange 64 extending in the opposite direction from that of flange 32 of cutting member 12 as viewed in FIGS. 1–3. Flange 64 also has a flat proximal side. The stylet 46 has a longitudinally extending groove or cavity 66 in the sidewall of the needle which is adapted to receive body tissue to be sampled. Stylet 46 is solid and circular in cross-section and is sized to be slidably received in the lumen 19 of cannula 18 as shown in FIGS. 1–3. The stylet is preferably made of stainless steel.

Housing 16, as also seen in FIGS. 11–14, has longitudinally extending upper and lower sides 67 and 68, and opposed sidewalls 69 and 70 providing a longitudinally extending chamber 72 for receiving the tissue cutting and stylet members 12 and 14. The housing 16 is generally rectangular in cross-section and completely encirles or surrounds the cutting and stylet members. The housing has a flange 74 at the proximal end and a flange 76 at the distal end which extend entirely around the housing as best seen is FIGS.12 and 13. Sidewalls 69 and 70 have a pair of grooves 78 and 80, respectively, which extend distally from flange 74. Groove 78 has proximal and distal end walls 81 and 82 which form stops engagable with stop 38 on the cutting member 12 to limit movement of the cutting member in both distal and proximal directions of movement. The groove 80 in wall 70 has proximal and distal end walls 83 and 84 which serve as stops for abutment stop 60 on stylet 14 to limit similar movement thereof. On the inner sides of the upper and lower walls 67 and 68 of the housing are a pair of rails 85 and 86, respectively, on which the actuators 22 and 48, respectively, slide when the cutting and stylet members 12 and 14 are moved in the housing. Housing 16 is also provided with a collar 87 at the distal end thereof which has a passage 88 connected with the chamber 78 to closely receive the cannula 18 is sliding relation.

As best seen in FIGS. 15 and 16, the cavity 66 of stylet 18 is spaced from but near the distal end or tip 47 of the stylet. The cavity 66 has opposed proximal and distal end walls 89 and 90 and may be formed by grinding or the like. When the cannula 18 is in its distal or forward most position with respect to the stylet 46, as in FIG. 1 and FIG. 15, the stylet completely covers the cavity 66 with the tip 20 of the cannula on a cylindrical distal end portion 91 of the cannula. With the cannula 18 and stylet 46 relatively positioned as in FIG. 1, they can be inserted into a desired location in the body tissue without coring tissue during the insertion. FIG. 16 shows the cannula 18 retracted or in its most proximal or rearward position with respect to the stylet 46 so that the cavity 66 is fully uncovered and the cannula is surrounding a cylindrical portion of the stylet which is proximal of the cavity. The outer surface of the bottom wall of the cavity 66 is arcuate or rounded as shown in FIG. 17.

When assembling the biopsy device 10, the distal tip 47 of stylet 46 is inserted into the proximal end of lumen 19 of cannula 18 and such that the guide 49 of the stylet actuator 48 enters the channel 29 of the cannula actuator 22. The stylet 46 may be moved distally in cannula 18 while slightly bending the stylet to allow the stylet guide 49 to move beyond the stops 42 and 44, without effecting a permanent bend in the stylet, and enterchannel 29. Alternately, the guide 49 may be positioned on the proximal side of the stops 42 and 44 and pushed distally through the stops where the stops are inclined as shown (FIG. 7) and the walls 26 and 28 of actuator 22 are somewhat resilient. With stylet 46 within the cannula 18, the two are inserted into the left end of housing 16 and through the distal opening 88 (FIG. 14) with the actuators entering the housing and with the housing rails 85 and 86 between the actuators. Next, the resilient spring members 36 and 58 may be pinched toward each other to move the abutments 38 and 60 inwardly past the housing end abutments 81 and 83. When released, the cannula and actuator members 12 and 14 are slidably disposed in housing 16 with the guide 49 entering the channel 29 of the cannula actuator and being longitudinally slidable.

In the asembled biopsy device 10, the cannula and stylet members 12 and 14 are limited in movement in the proximal direction by the engagement of the actuator stops 38 and 60 with the housing stops 81 and 83, respectively, as in FIG. 1. In FIG. 1 the members 12 and 14 are in the fully retracted or maximum proximal or rearward position. Also, in the fully retracted position, the stops 42 and 44 (FIG. 7) on the cannula actuator 22 are engaged by the stops 43 and 45 (FIG. 8) on the stylet actuator 48.

The movement of the cannula and stylet member 12 and 14 in the distal direction is limited by the engagement of the actuator stops 38 and 60 with the housing stops 82 and 84, respectively. Members 12 and 14 are shown in FIG. 3 in the maximum distal or extended position.

The stylet actuator stops 43 and 45 (FIG. 8) cooperate with the cannula actuator stops 42 and 44, respectively, to limit proximal movement of the stylet actuator relative to the cannula actuator to positively prevent the cannula tip 20 from moving distally of the distal tip 47 of the stylet 46. This ensures that the operator of device 10 cannot, under any circumstance, insert the device 10 into body tissue with the cannula tip distally of the stylet tip.

Whenever the actuators are positioned such that the actuator flanges 32 and 64 are substantially equidistant from the flange 74 of housing 16, such as shown in FIGS. 1 and 3, the cannula 18 covers the cavity 66 of the stylet as best seen in FIG. 15. Thus, the operator of the device 10 will readily known when the device can be inserted into a patient without coring tissue.

In operation, preparatory to insertion of the device 10 into the tissue of a patient, indicated at 94, the cannula and stylet members 12 and 14 are retracted or moved to their most proximal positions as shown in FIG. 1. In this condition, the friction bumps 40 and 62 of the actuators engage the proximal end of housing flange 74 to resist inadvertent distal movement of the actuators relative to the housing. In this condition, the cavity 66 is covered by the cannula 18. Since the walls of the actuators are slightly flexible, such resistive forces due to the bumps are overcome when manual forces are applied to the members to urge them into the housing 16.

With the members 12 and 14 positioned as shown in FIG. 1, the housing 16 may be grasped by the hand to move the distal tips 20 and 47 of the members 12 and 14 into the patient and up to that area of the body from which a sample is to be taken, such as indicated at 96. When the biopsy device is properly positioned in the patient, the housing may be held stationary with one hand while the stylet actuator 48 is moved distally to its full distal position as shown in FIG. 2 wherein the stop 60 engages housing stop 84 at the distal end of housing groove 80. During this movement, the cannula 18 and housing 16 remain stationary while the stylet 46 is moved distally relative to the cannula and into the tissue material from which a sample is to be taken. The engagement between the bump 40 and proximal end of housing 16 prevents any inadvertent movement of the cannula actuator at this time. In the position shown in FIG. 2, tissue material from which a sample is to be taken will extend into the cavity 66 and the condition of the cannula and stylet will appear as in FIG. 16, that is, with cavity 66 fully open. Next, while still holding the housing stationary in the same hand, the cannula actuator 22 is moved distally from its position in FIG. 2 to its position is FIG. 3, that is, to its full distal position wherein the cannula actuator stop 38 engages stop 82 at the distal end of the housing groove 78. During this movement the cutting end 20 of the cannula 18 cuts sample material that extends into the cavity 66 and returns the cannula 18 and stylet 46 to the positions indicated in FIG. 15 but now the cavity 66 will contain the severed tissue sample (not shown). The biopsy device 10 is then removed with the sample being maintained in the cavity 66 by the cannula 18. The cannula 18 may then be retracted or moved proximally relative to the stylet to open the cavity 66 and permit removal of the tissue sample for test purposes.

Because of the use of housing 16, the operation of the device 10 is simple and the risk of operating errors and inadvertent damage to the patient is reduced. Since housing 16 may be held stationary with one hand after the insertion of the device 10 into the patient, the housing provides a stable reference point with respect to the patient and for the subsequent movements of the cannula and stylet memebers 12 and 14 in properly obtaining the desired tissue sample. This method and operation of device 10 is simple in that after initial insertion of the device 10 while in the condition shown in FIG. 1, both actuators 22 and 48 are manually pushed forward, first the stylet actuator 48 and then the cannula actuator 22.

The biopsy device 10 may be operated in a somewhat different manner from that previously described herein. For example, the actuators 22 and 48 may be initially moved fully forward or to their most distal positions as shown in FIG. 3 and, while holding the actuators in these positions, inserting the cannula and stylet fully into the tissue to be biopsied such as shown in FIG. 3. Then, while maintaining the housing 16 and stylet 48 stationary, the cannula actuator 22 is moved proximally to its most proximal position such as to the position shown in FIG. 2. By moving the cannula in the proximal direction, the cavity 66 is exposed to allow tissue to enter the cavity. The next step is to move the cannula actuator 22 forward or distally while maintaining the stylet 46 and housing stationary to thereby cut body tissue and trap it in the cavity 66 of the stylet. While so trapped, the biopsy deivce is removed from the patient. This method is also simple since only cannula actuator 22 is moved after the device is inserted, that is, actuator 22 is first moved proximally to open the stylet cavity 66 and then it is moved distally to effect the cutting of the tissue.

In both of the above described procedures, the housing, after the device is initially inserted into the patient, remains stationary to limit the movements of the actuators in obtaining the desired biopsy specimen and to provide a stable reference point for indicating the relative positions of the cannula and stylet when in the patient.

Figure 19:
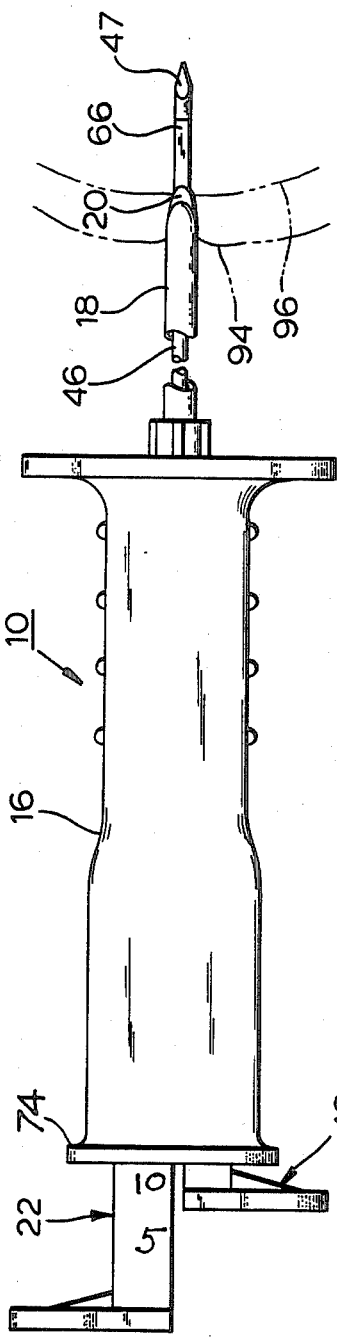
FIG. 19 is a plan view similar to FIG. 18 but with the stylet and cannula members in a different operating condition.
Figure 20:
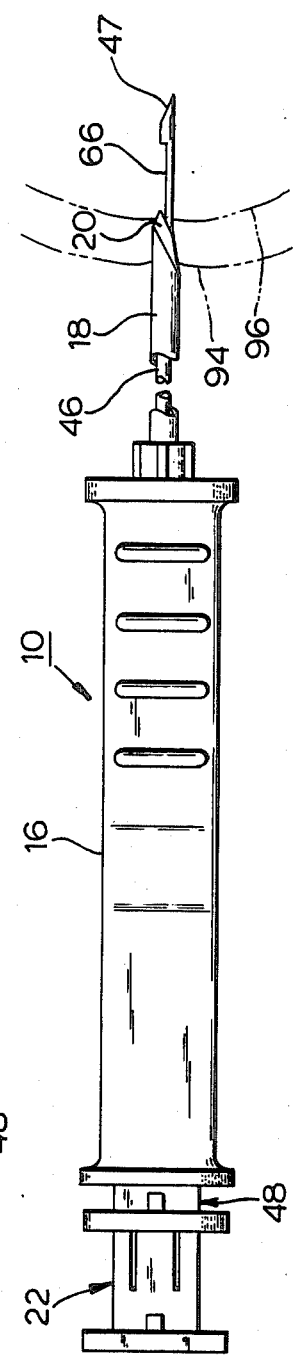
FIG. 20 is a bottom view of the biopsy device as shown in FIG. 19.

The biopsy device 10 may also be used to remove a biopsy specimen of smaller length than that obtained by the above two procedures. For example, with the biopsy device in the condition shown in FIG. 1, that is, with the cannula and stylet members 12 and 14 in the fully retracted or most proximal positions, the device is inserted into the patient to a point adjacent the tissue from which a sample is to be taken. After insertion and while holding the actuators 22 and 48 stationary, the housing 16 is moved a selected amount proximally relative to the actuators. A scale 98 (FIGS. 5, 18 and 19) is provided on the cannula actuator 22 to indicate the amount of movement of the housing from its position in FIG. 1 to its position in FIG. 18. For example, the scale may be in millimeters. Next, while maintaining the housing 16 and cannula actuator 22 stationary, the stylet actuator 48 is moved proximally into housing 16 as far as it will go, such as shown in FIG. 19. The distal advancement of the stylet actuator 22 is stopped as a result of the engagement between the housing stop 84 and stylet actuator stop 60. Since the housing 16 had been moved proximally, the advancement of the stylet actuator 22 relative to the cannula actuator 22 is reduced. This means that the length of the cavity uncovered by the cannula 18 (FIG. 19) is less than the full length of the cavity and is represented by the position of the housing flange 74 on the scale 98. With the device 10 in the condition shown in FIGS. 19, and 20, the cannula actuator 22 is moved distally until it is stopped by the engagement between stop 38 on cannula actuator 22 and stop 82 on housing 16. This latter movement of the cannula cuts the body tissue and closes cavity 66 so that the device 10 may be removed from the patient along with the sample. In this case, the length of the sample will be less than that obtained when the full length of the cavity 66 is used to receive sample tissue.

FIGS. 21–23 illustrate an embodiment in which the biopsy device 10 is connected to a hand grip 100 so that the device 10 may be readily used with one hand thereby freeing the other hand for other work. Hand grip 100 includes an elongate platform 102 which supports the housing 16. The platform extends between the housing flanges 74 and 76 to provide a tight fit therebetween. The platform 102 includes a flat bottom supporting wall 104, a pair of opposed sidewalls 106 and 108 which respectively engage the opposed sides 69 and 70 of the housing. These sidewalls 106 and 108 are curved as seen in FIGS. 22 and 23 so as to extend slightly over the upper wall 67 of the housing to firmly hold the housing in place on the platform. At the distal end of platform 102 are a pair of integral upstanding walls 110 and 112 that engage the proximal side of the housing flange 76. Connected to the platform is a depending handle 114 adapted to be gripped by the hand. In this way, the handle 114 may be gripped by the hand and the thumb used to operate the actuators 22 and 48 from the proximal end of the device 10. The handle 114 has a flat, relatively thin web 116 with a wider peripheral border 118. The border widens near platform 102 to form a thumb rest area indicated at 120. The plane of the web 116 is closer to the plane of sidewall 106 than to the plane of sidewall 108 to allow a more natural and comfortable positioning of the thumb.

The hand grip 100 is preferably a single piece molded plastic member of relatively rigid plastic. The plastic should be flexible enough to allow the housing 16 to be manually inserted onto the platform 104 when forced between the sidewalls 106 and 108. These sidewalls should be resilient enough to firmly grip the housing during use. The handle 100 and device 10 may be assembled by first forcing the narrow distal portion of housing 16 between the resilient walls 106 and 108 of the handle. Then the housing 16 may be moved distally until the housing flange 76 passes the distal end of the platform 102. The sidewalls then resiliently engage the enlarged proximal portion of the housing.

The device 10 may be removed from the handle 100 by holding housing flange 76 stationary with one hand and gripping handle 100 by the other hand. Then, forcing the distal end of platform 102 downwardly and angularly away from the housing 16, that is, tilting the distal end of the platform 102 downwardly and away from the distal end of the housing. As the platform moves angularly away from the housing, the wider portion of the housing is forced through the resilient sidewalls 106 and 108 of the handle to free the device 10. The handle 100 may be repeatedly used with different medical devices such other biopsy devices similar or identical to device 10.

The actuators 22 and 48, the housing 16, and the hand grip 100 may be formed or molded or a relatively rigid plastic such as an acrylonitrile butadiene styrene (ABS), a polycarbonate, a polysulfone or other similar plastic.

When operating the device 10 with the handle 100 attached, the steps and movements of the parts may be the same as those previously described herein except that the thumb can be used to operate the actuators.

The housing 16 as constructed and shown in symmetrical so that the actuators 22 and 48 can be assembled with housing 16 even when the housing is rotated 180° on its longitudinal axis from the orientation shown in the drawings.

As various changes could be made in the above described construction and method without departing from the true spirit and scope of the invention, it is intended that all matter contained in the above description and shown in the accompanying drawings be interpreted as illustrative.

What is claimed is:

1. A biopsy device comprising first and second members cooperable to effect the cutting of body tissue in the taking of a tissue sample from a patient, said first member comprising an elongate cannula having a distal end for cutting body tissue and an elongate actuator connected thereto at the proximal end thereof for moving said cannula, said second member including an elongate stylet slidable in said cannula and having a distal end for piercing body tissue and a cavity adjacent said distal end for receiving body tissue, and an actuator connected thereto at the proximal end thereof for moving said stylet, and an elongate housing having a passage therethrough for receiving said first and second members for longitudinal sliding movement relative thereof, said actuators being slidable in parallel side-by-side relation with a portion of each of said actuators longitudinally slidable distally into and proximally out of the proximal end of said passage said cannula and stylet being adapted to effect the cutting of tissue in response to predetermined relative movement thereof when body tissue is in said cavity, said first and second members being movable such that the proximal ends of said actuators are equidistant from the proximal end of said passage with said distal end of said cannula covering said cavity and proximal of said distal end of said stylet.

2. A biopsy device comprising a tissue cutting member including an elongate tissue cutting cannula having a lumen extending therethrough and open at its proximal and distal ends, and an elongate cannula actuator connected adjacent the proximal end of said cannula for moving said cannula, the distal end of said cannula being sharp for cutting tissue, a stylet member including an elongate stylet slidable in said lumen and having a pointed distal end for piercing tissue, said stylet having a longitudinally extending cavity therein near the distal end thereof, and an elongate stylet actuator connected to the proximal end of said stylet for moving said stylet means for limiting relative longitudinal movement between said actuators for preventing the distal end of said cannula from extending distally beyond the distal end of said stylet, a housing receiving said cutting and stylet members for longitudinal sliding movement relative to said housing with portions of said cannula and said stylet movable into and out of the distal end portion of said housing and with portions of both of said actuators movable into and out of the proximal end portion of said housing, said portions of said actuators having longitudinal axes in parallel spaced relation with each other and with the longitudinal axis of said housing, and means for limiting longitudinal movement of said actuators relative to said housing, said cutting and stylet members being movable such that when the proximal ends of said actuators are equidistant from the proximal end of said housing the distal end of said cannula is proximal of the distal end of said stylet and covers said cavity.

3. A biopsy device comprising a tissue cutting member including an elongate tissue cutting cannula having a lumen extending therethrough and open at its proximal and distal ends, and an elongate cannula actuator connected adjacent the proximal end of said cannula for moving said cannula, the distal end of said cannula being sharp for cutting tissue, a stylet member including an elongate stylet slidable in said cannula lumen and having a pointed distal end for piercing tissue, said stylet having a longitudinally extending cavity in the sidewall thereof spaced from but near the distal end thereof for receiving sample material, and an elongate stylet actuator connected to the proximal end of said stylet for manually moving said stylet, means for limiting relative longitudinal movement between said actuators including means for preventing the distal end of said cannula from extending distally beyond the distal end of said stylet, and a housing for receiving said cutting and stylet members for longitudinal sliding movement relative to each other and to said housing with said cannula and said stylet extending concentrically from the distal end of said housing, portions of said actuators extending in parallel relation to each other and movable within said housing, said actuator portions being movable out of said housing with the proximal ends of said actuators longitudinally spaced from the proximal end of said housing, means for limiting relative longitudinal movement between said actuators and said housing so that said actuators are movable a predetermined amount relative to said housing, said members being sized so that said distal end of said cannula is proximally of the distal end of said stylet and said cannula is covering said cavity when the proximal ends of said actuators are substantially equidistant from the proximal end of said housing, said cannula exposing said cavity when the proximal ends of said acuators are predeterminately longitudinally spaced from each other, said cannula being movable in a distal direction relative to said stylet for cutting sample material when extending into said cavity.

4. The device of claim 3 wherein said housing includes a pair of opposed sidewalls and upper and bottom walls connected to said sidewalls and providing a passage for receiving said members, and said means for limiting relative longitudinal movement between said actuators and said housing include a first pair of abutments on the inner sides of said opposed sidewalls respectively, and a second pair of resiliently outwardly urged abutments respectively on said actuators movable inwardly for inserting said actuators past said first pair of abutments and into said passage when inserting said actuators into said housing so that said first pair of abutments are proximally of said second pair of abutments, said second pair of abutments being respectively engageable with said first pair of abutments to limit proximal movement of said actuators relative to said housing.

5. The device of claim 4 wherein said housing has a third pair of abutments on the inner sides of said opposed sidewalls, respectively, which are distally spaced from said first pair of abutments, said second pair of abutments being engagable with said third pair of abutments to limit the distal movement of said actuators relative to said housing.

6. The device to claim 5 wherein said actuators include resilient portions, said second pair of abutments being disposed respectively on said resilient portions.

7. The device of claim 6 wherein said resilient portions include a another pair of abutments respectively which are proximally of said second pair of abutments and are adapted to frictionally engage said housing effecting reistance against movement of said actuators in a distal direction from a position in which the distal ends of said actuators are spaced a maximum distance proximally from said housings.

8. The device of claim 7 wherein said housing completely surrounds said members including said actuators.

9. The device of claim 3 further including a handle removably connectable to said housing and having a hand grip for holding the device with one hand.

10. The device of claim 9 wherein said handle is a single-piece member having a platform for receiving said housing, opposed resilient sidewalls connected to said platform for resilient engaging opposed sides of said housing, and a hand grip extending downwardly and proximally from said housing when said housing is connected to said handle such that the proximal ends of said actuators can be moved distally from a first position in which they are proximal of the proximal end of said housing by the thumb.

11. A method of taking a biopsy sample from a patient comprising the steps of providing a biopsy device having a housing with a passge therethrough, a cannula member slidable in the housing passage including a cannula having a distal tissue cutting end and an elongate actuator connected at the proximal end thereof for moving the cannula, a stylet member slidable in said housing passage including a stylet having a tissue piercing distal end and a tissue receiving cavity adjacent the distal end, and an elongate actuator connected at the proximal end thereof for moving the stylet, both of the actuators being slidable distally into and proximally out of the proximal end portion of the housing passage, inserting the cannula and stylet into the patient with the cavity in the stylet closed by the cannula, while holding the housing substantially stationary moving one of said actuators in one direction relative to the other of said actuators and said housing to open the cavity and allow body tissue to enter the cavity, while holding the housing and stylet actuator substantially stationary moving the cannula actuator distally relative to said stylet actuator to effect cutting body tissue extending into the cavity and closure of the cavity, and withdrawing the cannula and stylet from the patient with the sample in the cavity, the proximal ends of said actuators being substantially equidistant from the housing during said step of inserting the cannula and stylet into the patient.

12. The method of claim 11 wherein said one actuator is said stylet actuator and said one direction is the distal direction.

13. The method of claim 12 further including the step, after the step of inserting the cannula and stylet into the patient and before the step of moving said one actuator, of moving the housing a selective distance proximally while maintaining said actuators substantially stationary to provide a sample of tissue of less length than the maximum possible length of tissue obtainable by the device.

* * * * *